United States Patent [19]

Crawford et al.

[11] Patent Number: 4,994,965
[45] Date of Patent: Feb. 19, 1991

[54] METHOD FOR REDUCING MOTION INDUCED IMAGE ARTIFACTS IN PROJECTION IMAGING

[75] Inventors: Carl R. Crawford, Milwaukee; Norbert J. Pelc, Wauwatosa, both of Wis.

[73] Assignee: General Electric Company, Milwaukee, Wis.

[21] Appl. No.: 276,249

[22] Filed: Nov. 23, 1988

[51] Int. Cl.⁵ .................................... G06G 7/60
[52] U.S. Cl. ............................ 364/413.15; 324/309; 378/95
[58] Field of Search ............... 364/413.15; 324/309; 128/653 R; 378/4, 95, 901

[56] References Cited

U.S. PATENT DOCUMENTS

| | | | |
|---|---|---|---|
| 4,144,569 | 3/1979 | Wagner | 364/413.19 X |
| 4,567,893 | 2/1986 | Charles et al. | 324/309 X |
| 4,568,880 | 2/1986 | Sugimoto | 324/309 |
| 4,580,219 | 4/1986 | Pelc et al. | 364/414 |
| 4,720,678 | 1/1988 | Glover et al. | 324/309 |
| 4,727,882 | 3/1988 | Schneider | 324/309 X |
| 4,751,462 | 1/1988 | Glover et al. | 324/309 |

Primary Examiner—Jerry Smith
Assistant Examiner—Steven Kibby
Attorney, Agent, or Firm—Quarles & Brady

[57] ABSTRACT

A method of reducing image artifacts in tomographic, projection imaging systems due to periodic motion of the object being imaged includes the acquisition of a signal indicative of the periodic motion. This signal is used to identify a quiescent period in the periodic motion so that the acquisition of projection data may be coordinated to be centered within the quiescent period. The sequence of the angles at which projection data is acquired is controlled so that the primary axis of periodic motion is perpendicular to the axis of projection at the center of the quiescent period. Multiple periodic signals may be coordinated by awaiting their best alignment over a fixed number of cycles of one of the periodic motions.

8 Claims, 4 Drawing Sheets

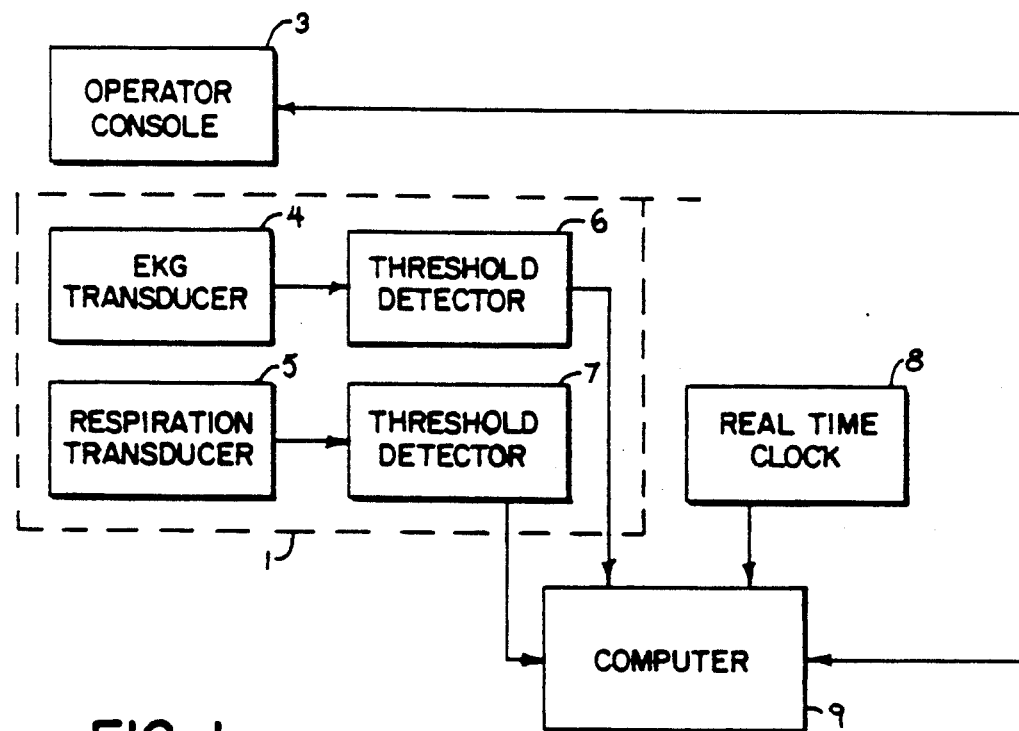
FIG. 1
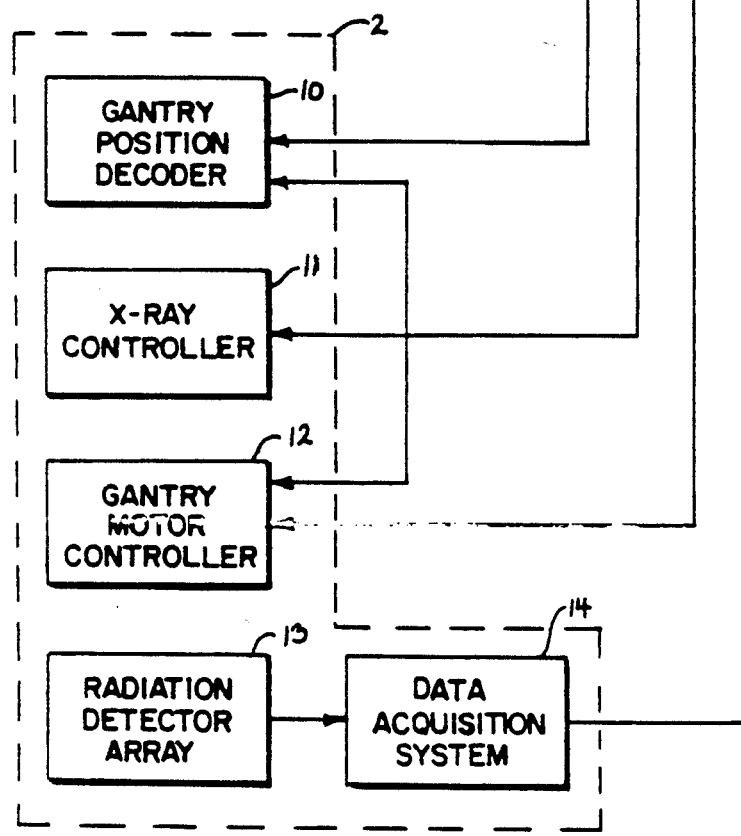

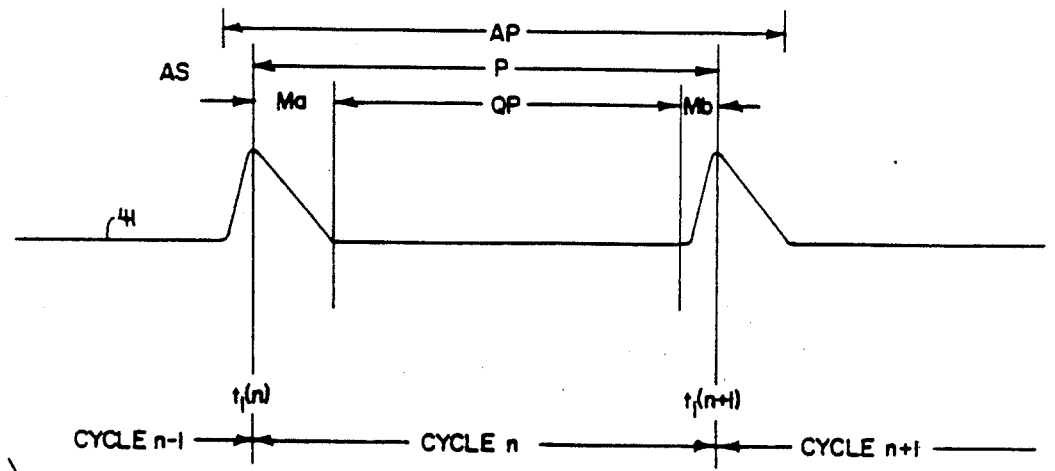
FIG. 3
FIG. 4
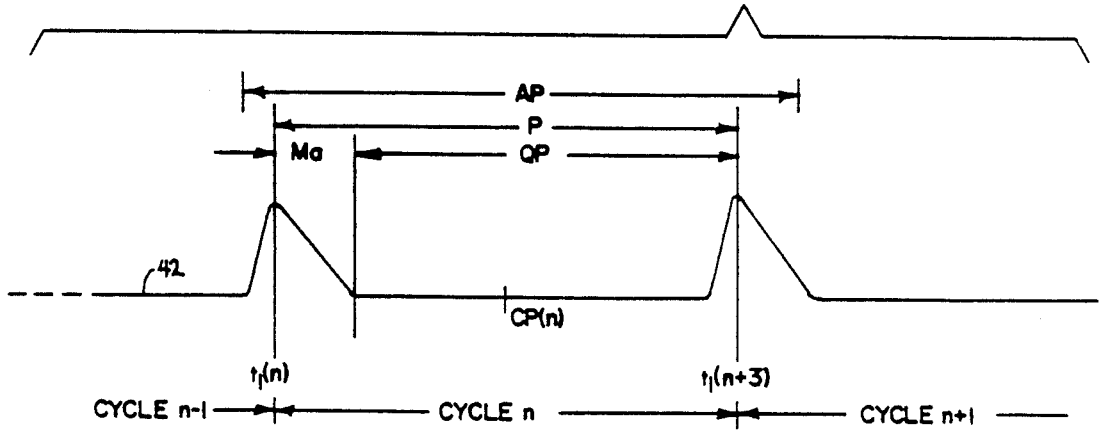
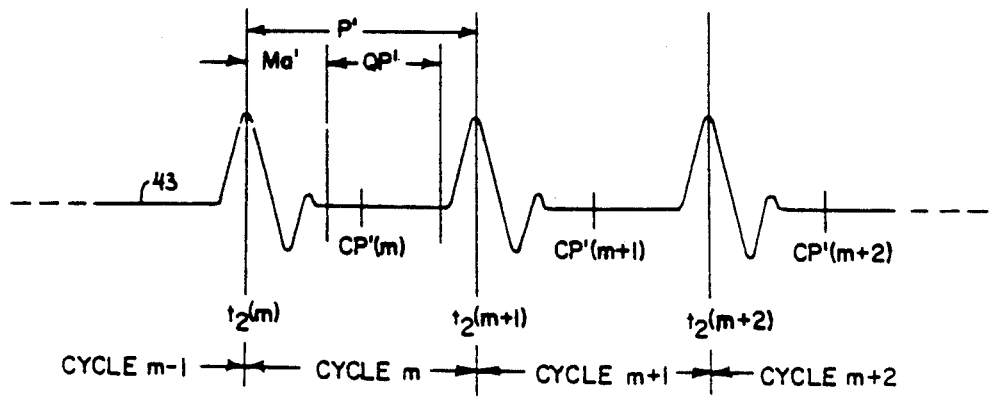

METHOD FOR REDUCING MOTION INDUCED IMAGE ARTIFACTS IN PROJECTION IMAGING

BACKGROUND OF THE INVENTION

This invention relates to a computed tomography imaging method to reduce motion artifacts resulting from substantially periodic motion of the object being imaged. More specifically, the invention relates to an image artifacts suppression method for use with projected image techniques such as transmission computed tomography (CT) and emission computed tomography. As used herein, transmission imaging refers to imaging by detecting radiation transmitted through the body being imaged, and emission imaging refers to imaging by detecting radiation emitted from the body being imaged, e.g., such as that being emitted by radiopharmaceutical isotopes.

In one embodiment of a transmission computed tomography system, an x-ray source is collimated to form a fan beam directed along a slice plane through an imaged object to a series of x-ray detectors oriented within the slice plane. Each detector measures the intensity of transmitted radiation along a ray projected from the x-ray source to that particular detector element. The intensity is dependent on the scattering and absorption of the x-ray beam along that ray by the imaged object. The detectors are organized along an arc each to intercept x-rays from the x-ray source along a different ray of the fan beam and hence together to collect data for a complete projection. A given projection collected in this manner is identified by the fan beam's center most ray, termed the projection axis. The x-ray source and detectors are then rotated within the slice plane around the object being imaged so that the principal axis of the fan beam intercepts the object being imaged at a new angle The process is repeated to collect a number of projections each along a different such angle to form a tomographic projection set. The multiple projections of this set are then reconstructed through reconstruction algorithms known in the art to provide a tomographic view in the slice plane of the object being imaged.

Emission computed tomography may be performed in a similar manner. Briefly, a set of detectors are again rotated around the imaged object within a slice plane. The detectors receive radiation not from an external x-ray source, but rather from radioactive isotopes within the object itself. The radiation received by the detectors reveals scatter and absorption of the emitted radiation and also relative concentrations of the radioactive source within the object being imaged. The detector array receives a different projection as its position is moved to different angles with respect to the imaged object all within the slice plane. Each projection may be identified by the principal axis of the detector array, also termed the projection axis.

The acquisition of a computed tomographic image may take a significant amount of time. In both transmission and emission tomography, the need for multiple projections usually requires physical movement of the detector array and/or the x-ray source. Efforts at speeding the acquisition of projection data are limited by the speed with which the mechanical elements of the acquisition system, the detector and/or the x-ray source, may be relocated around the object to be imaged. Attempts to reduce scan times beyond certain limits can also adversely affect signal to noise ratio in the reconstructed image. Signal to noise ratio is directly related to the emitted or transmitted fluence during the acquisition of a given projection, and the fluence is effectively reduced at higher scan rates.

If the imaged object moves during the acquisition of the complete set of projections required for image reconstruction, the resulting image may show certain motion induced artifacts in the form of loss of resolution, streaking, "bubbling" in the area of dense objects, or doubling of moving objects termed "ghosts". Ghosts are more common when the motion is substantially periodic.

Most physiological motion is not perfectly periodic. The period may change over time and the moving object may not return to the same position even at identical points within each cycle. For the purposes of this discussion, the former criterion will be termed temporal periodicity and the latter criterion will be termed spatial periodicity.

Considerable effort has been invested in reducing the scan times required for a tomographic reconstruction. Practical scan times have been reduced from minutes to a few seconds over the last several years. Nevertheless, the periods of cardiac, peristaltic and respiratory motion are such that some motion is likely during data acquisition even under present shortened scan times. A number of methods are used to minimize such motion artifacts. Scanning protocols may be adopted to limit the motion: patients are instructed to lie still and to hold their breath during the scan, patient restraints and supports limit general muscular motion, and peristaltic motion may be reduced with drugs. These techniques are only partially successful and are often not feasible as in the case where the patient is traumatized or where scanning must be performed in an emergency situation.

As an alternative, gating techniques which acquire partial sets of projections timed with the periodic physiological activity, such as a breath or a heart beat, have been used with some success. In these techniques, the acquisitions of a full set of projections for an image is performed over a number of cycles of the physiological motion. Typically the projections are continuously acquired and then "sorted", according to the phase of the cycle during which they were taken to construct separate images for each phase of the periodic motion. With cardiac gating, for example, the EKG signal is used to coordinate the acquisition of data with the phase of the cardiac cycle, to obtain separate images at each phase of the beating heart after a number of cycles or beats of the heart.

Although the above described gating techniques allow for images with reduced motion artifacts, these techniques have some drawbacks. A given image images takes longer to obtain because data can be acquired only during a portion of each motion cycle. For reasonable acquisition periods, there will be missing projections from each projection set as a result of a failure of a particular projection axis to coincide with the proper motion phase during the acquisition time and less than ideal projection data will have to be used. Finally, because many cycles are required to obtain the entire projection set for an image, this technique is particularly susceptible to spatial non-periodicity in the physiological motion.

SUMMARY OF THE INVENTION

The present invention relates to an imaging method to reduce motion artifacts during a single scanning period when the motion is substantially periodic. More specifically, the present invention times the acquisition of data to occur at a point determined to result in minimized motion artifacts. Further, the starting angle of the projections and the sequence of the projections acquired is controlled to reduce motion artifacts.

A general object of the invention is to maximize the useful projection data that may be acquired during a given cycle of spatially non-periodic motion of the imaged object. This is performed by centering the period of least motion within the data acquisition period so that motion artifacts which result from spatial nonperiodicity are minimized. These artifacts are more pronounced if data is acquired during a period which straddles periods when the object is moving.

Yet another object of the invention is to minimize the effects of motion itself on the acquired image. It has been experimentally determined that motion occurring at the ends or beginning of the scan have the least effect on the image with regard to motion artifacts. By centering the quiescent period of the imaged object's cycle within the acquisition window, the intervals of motion are displaced to the ends of the acquisition time resulting in fewer motion artifacts.

A further object of the invention is to coordinate the projection axes of the acquired data with the direction of principal axis of the motion to further minimize the effect of any motion and spatial non-periodicity. It has been determined that motion substantially parallel to the axis of projection results in a less pronounced image artifact then motion substantially perpendicular to the projection axis. Accordingly, the sequence and angles of the projections are timed so that motion that occurs occurs during periods when the projection is substantially parallel to the direction or principal axis of the motion.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 1 is block diagram of CT control system useful for practicing the invention;

FIG. 3 is a graphic representation of a respiratory transducer signal;

FIG. 4 is a graphic representation of a respiratory transducer signal juxtaposed with a EKG waveform;

DESCRIPTION OF THE PREFERRED EMBODIMENT

Figure 2:
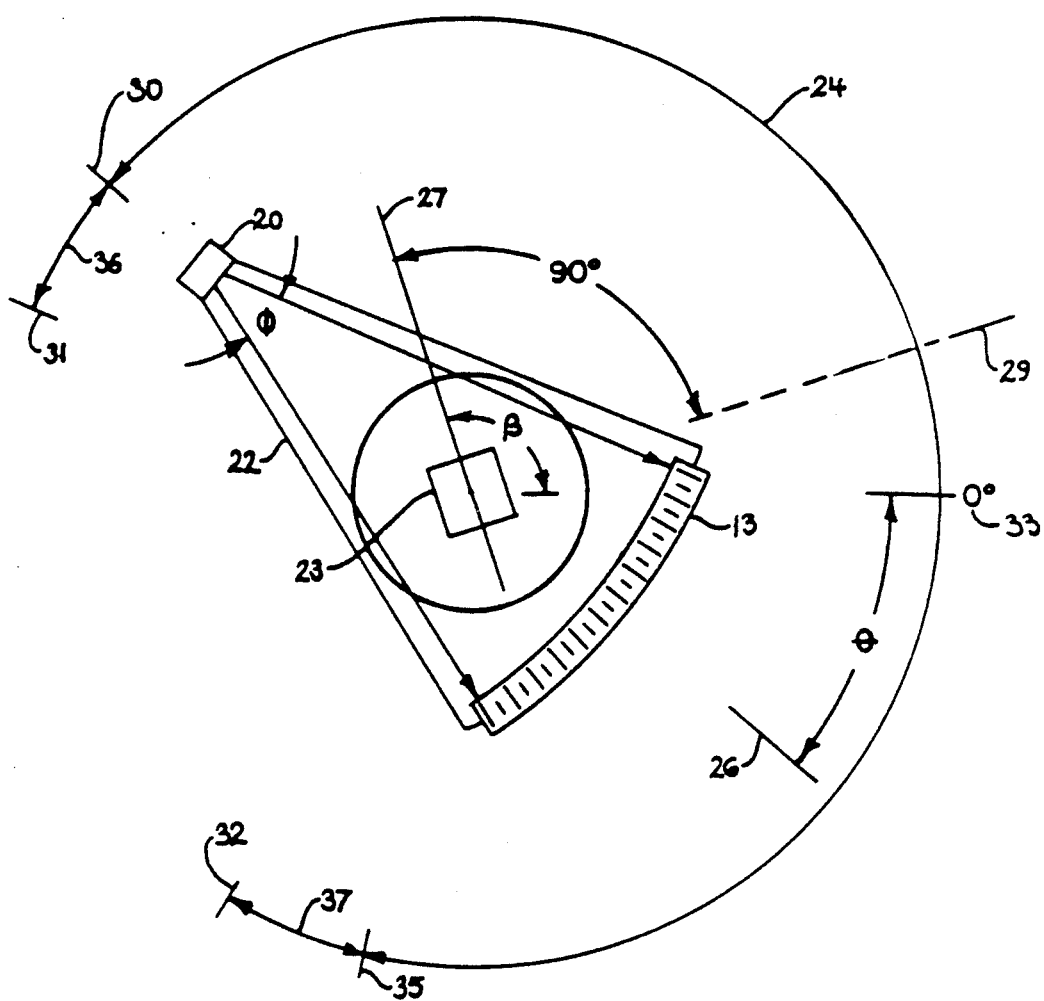
FIG. 2 is a pictorial representation of a CT gantry showing the relative angles associated therewith.

Referring to FIG. 2, there is shown a schematic representation of a CT gantry 22 representative of "third generation" CT equipment construction suitable for use with the preferred embodiment of the invention. Said gantry 22 comprising an x-ray source 20 oriented to project a fan beam of x-rays of angular divergence $\phi$ through imaged object 23 to detector array 13. The angle of the gantry with respect to the imaged object is termed $\theta$ and is arbitrarily referenced to 0° at angle 33 for purposes of discussion. $\theta$ may vary by 360° or more in a typical system in order to acquire projection data. A "fourth generation" CT system (not shown) may be constructed of fixed multiple detectors receiving a fan beam of x-rays from a rotating x-ray source. The present invention is applicable equally to such a fourth generation machine. In this case, $\theta$ would be simply the angle of the movable x-ray source with respect to the imaged object.

Imaged object 23 has a periodic motion which is substantially parallel to the principal axis 27 oriented at angle $\beta$. Arc 24 represents the minimum preferred subtended angle of acquisition for the reconstruction of a CT image and is typically 180° plus the angle of the fan beam $\phi$. The midpoint of this acquisition angle is positioned with respect to the imaged object 23 in accordance with the present invention as will be described further below.

Referring now to FIG. 1 there is shown a block diagram of the preferred control system of a CT imaging system which embodies the present invention. The CT control system shown includes three sections: the patient monitoring circuitry 1, which provides information related to the patient respiration, heartbeat or other periodic physiological activity; the CT interface circuitry 2, which controls the operation of the components of the CT machine including, the x-ray source, the gantry position and the detector array; and, the operator input console 3, which allows the operator or radiologist to enter parameters used in practicing the invention and to receive data from the CT machine. Each of these sections connects with a computer 9 which is in turn connected to a real time clock 8 that produces timing information required for the control sequences.

The patient monitoring section 2, comprises two transducers: an electrocardiograph (EKG) 4, providing signals relating to the beating heart, and a strain gauge chest belt 5, which provides a signal indicating respiration. One or both of these transducers may be used and transducers for measuring other substantially periodic motions associated with the imaged object may be substituted for these devices. Additional transducers also may be added according to the method of the present invention as will be apparent to those skilled in the art.

Each transducer 4 and 5 is connected to a threshold detector 6 and 7 respectively, which produces a pulse upon the occurrence of a landmark portion of the transducer signal. A landmark is a point in the signal which identifies the start of one cycle of periodic motion. The threshold detectors 6 and 7 are low pass filters followed by an adjustable voltage comparator. Upon the occurrence of each pulse, the computer 9 reads the real time clock 8 and stores the time associated with each pulse from threshold detectors 7 and 6 in the array variables $t_1(n)$ and $t_2(m)$ respectively. n and m are index variable indicating the relative cycle of the periodic motion being measured.

The CT gantry control section 2 consists of a gantry position encoder 10 which provides data as to the angle of the CT gantry, i.e. the projection axis, with respect to the patient table, to be described in more detail below. An x-ray tube controller 11, energizes and de-energizes the x-ray tube and hence controls when projection data is available. A gantry motor controller 12 in conjunction with a gantry position encoder 10 allows for the precise location of the initial gantry position prior to acquiring data and allows for the control of the speed and direction of the sequence of projection axes obtained during data acquisition. The detector array 13 receives and detects the magnitude of the projected image resulting from the transmission of x-rays through the imaged object, or in the case of emission tomography, the radiation emitted from the radiopharmaceutical isotopes within the imaged object. The signals from the detector array 13 are sampled and digitized by data acquisition system 14 for processing by computer 9 according to known reconstruction algorithms.

The operator console 3 is generally a CRT display and keyboard which allows the operator to enter parameters for the scan and to display the reconstructed image and other information from the computer 9.

Referring to FIG. 3 there is shown, plotted against time, a representative signal 41 from the respiratory transducer 5. AP is the acquisition period derived by multiplying the maximum gantry rotational rate in seconds per degree by the minimum acquisition angle 24 as previously described in FIG. 2. P is the period of the respiratory motion for a given cycle. QP is a quiescent period, determined as a percentage of P. Times $t_1(n)$ and $t_1(n+1)$ are the absolute times of the signals from the threshold detector and $t_1(n)$ is the current such pulse delineating the beginning of cycle n of the respiratory motion $M_a$ is the time, as a percentage of the total period P, between the trigger pulse $t_1(n)$ and the beginning of the quiescent period QP. Values $M_a$ and QP are typically chosen by the operator based on prior knowledge of the physiology of the motion. Such knowledge may be obtained from medical studies of normal physiology or by studies performed with other imaging modalities such as ultrasound or conventional fluoroscopy. P varies slightly from cycle to cycle and hence may be derived for the purposes of the following formulas from a rolling and weighted average of the lengths of previous periods as measured by the signals from the threshold detector 6. In the preferred embodiment, P for the current cycle n is set equal to P for the previous cycle $n-1$.

Extensive computer simulation has suggested that if motion is to occur during the acquisition of data for a tomographic reconstruction, the motion should be positioned in time to occur at the beginning or end of the acquisition period AP. This differs from the prior art which initiates the acquisition period AP at the beginning of the quiescent period QP. Artifacts so positioned at the ends of the scan may be further reduced by the use of "half scan" or "underscan" techniques, the latter as disclosed in U.S. patent application No. 4,580,219, issued Apr. 1, 1986 and entitled "Method for Reducing Image Artifacts due to Projection Measurement Inconsistencies", and incorporated herein by reference. A half scan technique is described in "Optimization of Short Scan Convolution Reconstruction in Fan Beam CT", *Internal Workshop on Physics and Engineering in Medical Imaging*, 1982, p.199. Both techniques apply reduced weighting factors to projection data acquired at the beginning and end of a scan.

In the present invention, the quiescent period QP is centered within the acquisition period AP by initiating the scan for cycle $n+1$ at acquisition start time $AS = t_1(n) + P + M_a - \frac{1}{2}(AP - QP)$. In situations where the period of the motion P is less than the acquisition period AP, the start of acquisition will begin prior to pulse $t_1(n+1)$.

Further studies have indicated that if motion is to occur during the acquisition of projection data, the major component of the motion should be oriented, to the extent possible, along the projection axis of the data then being acquired. Prior to beginning the acquisition of data, therefore, the gantry 22, as shown in FIG. 2, is positioned so that motion of the imaged object 23 along axis 27, occurring during the acquisition time AP, will occur substantially parallel to the direction of the projection axis 26. This is accomplished by centering the acquisition angle 24 along an axis normal to the principal axis of the imaged object's motion 29. Referring again to FIG. 2, it may be seen that both acquisition arcs 24 and 25 meet the condition of being centered at an angle normal to the principal axis of the object's motion 27.

Centering of the acquisition arc 24 on an angle normal to the principal motion of the imaged object 29 ensures that any motion occurring occurs as close as possible to the ends of the scan time if the quiescent period QP has been centered within the acquisition time AP as has been described above.

Referring to the acquisition angle 24 in FIG. 2, scanning begins, for motion in the clockwise direction, when the gantry is at angle 30 and continues until it reaches angle 35. To accommodate the time required for the gantry to accelerate, the gantry is positioned prior to the scan at angle 31 for clockwise direction or angle 32 for counterclockwise rotation. Arcs 36 and 37 are thereby allowed for acceleration of the gantry. The time required for the gantry to accelerate through arc 36 or 37 is termed the warm-up time and is subtracted from the acquisition start time AS as calculated above to yield motion start time MS.

The gantry starting positions 31 or 32 are obtained by use of the gantry position encoder 10 and the gantry motor controller 11 which permit the gantry to be repositioned after each scan. The angles 31 and 32 shown in FIG. 2 are calculated by subtracting one-half of the total acquisition angle 24, plus the acceleration angle 37 or 37 from the motion normal angle 29 which is supplied by the operator and based on independent knowledge of the principal axis of motion of the imaged object.

The use of the present invention to coordinate data acquisition with two periodic physiological motions is more complicated and will now be described. Referring to FIG. 1, two signals may be received from two transducers, an EKG transducer 4 and a respiratory transducer 5 in the preferred embodiment. Sample transducer waveforms 42 and 43 are shown in FIG. 4. Referring now to FIG. 4, waveform 42 has a period of P during cycle n measured between time $t_1(n)$ and time $t_1(n+1)$ which represent readings from the real time clock taken on the rising edge of pulses from threshold detector 7. A center time CP(n) for quiescent period QP during cycle n for waveform 42 is calculated according to the formula $CP(n) = t_1(n) + M_a + \frac{1}{2} QP$, where N and QP are percentages of P which, as before, is determined from the previous P measurements.

Waveform 43 has a period of P' during cycle m measured between time $t_2(m)$ and time $t_2(m+1)$ which represent readings from the real time clock taken on the rising edge of pulses from threshold detector 6. Time periods $M_a'$ and QP', expressed as a percentage of P', have been selected by the operator based on independent knowledge of the physiology of the motion. In a like manner, CP'(m) is calculated for waveform 43 according to the formula $CP'(m) = t_2(m) + M_a' + \frac{1}{2} QP'$.

In the preferred embodiment, prior to each scan, a number of center points for each waveform 42 and 43 are estimated (CP(n), CP(n+1)...),(CP'(m),CP'(m+1)...) for a period of time into the future using the formula CP(n)=CP(n-1)+P and CP'(m)=CP'(m-1)+P' where P and P' are rolling averages of the respective waveform periods computed as of $t_1(n-1)$ and $t_2(m-1)$ respectively. The number of such center points that are calculated is bounded by the acceptable time between acquisitions of projections. Generally more pairs will permit better alignment between the two periodic but typically non-synchronous motion cycles.

Each center point for waveform 42 is compared to all center points for waveform 43 to identify the period n during which CP(n) is closest in time to any other measured center point for waveform 43. This identified period is selected for the acquisition of data and the gantry is put into motion at the motion start time for the identified cycle of waveform 42 as calculated above for the single transducer case. This procedure may be readily expanded to coordinate additional substantially periodic physiological motions by the use of additional transducers, as would be apparent to one skilled in the art.

Figure 5:
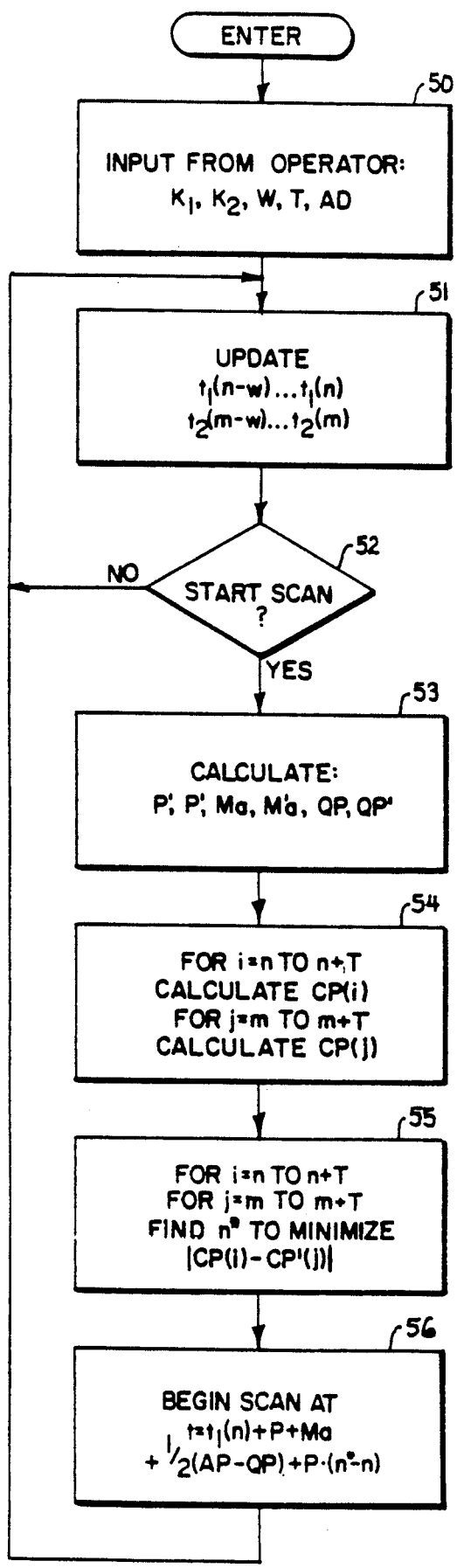
FIG. 5 is a flowchart of a method for determining acquisition start times.

Referring to FIG. 5 there is shown a more detailed flow chart illustrating the process of coordinating the acquisition start time with several physiological motions. The first step, 50, requires operator selection of parameters $k_1$, $k_1'$, $k_2$ and $k_2'$, from which $M_a$, $M_a'$, QP and QP' are determined according to the formulas: $M_a = k_1 P$, $M_a' = k_1' P'$, $QP = k_2 P$ and $QP' = k_2' P'$. The operator also selects value w which determines the number of cycles used to develop rolling averages value for P and P', and value T which controls how many future cycles will be examined to coordinate the two physiological motions.

At step two 51, time values $t_1(n-w)$ ... $t_1(n)$ and $t_2(m-w)$ ... $t_2(m)$ are collected. At step three 52, the program determines whether a initiate scan signal has been received from the operator. If a initiate scan signal has been received, the program proceeds to step four. If an initiate scan signal has not been received, the program returns to step two 50 to update the above described time values. These values $t_1$ and $t_2$ together with the parameters entered by the operator in the step one, 50, are used in step four, 53, to calculate the rolling average of the period of both the respiratory and cardiac motions P and P' respectively according to the formulas: $P = (t_1(n) - t_1(n-w))/w$ and $P' = (t_2(m) - t_2(m-w))/w$ where m is the cycle of the cardiac motion immediately preceding cycle n of the respiratory motion. $M_a$, $M_a'$, QP, and QP' are also calculated based on the respective rolling average periods P and P' and the operator supplied parameters as given above.

In step five, 54, center points for the quiescent periods of the respiratory and cardiac motion CP and CP' are calculated for the next T cycles of both motions according to the following formula: $CP(i) = t_1(n) + M_a + \frac{1}{2} QP + (P \cdot (i-n))$ and $CP'(j) = t_2(m) + M_{a'} + \frac{1}{2} QP' + (P' \cdot (j-m))$ where i is a cycle number from n to n+T and j is a cycle number from m to m+T', where T' equals $T \cdot (P/P')$ rounded up to the nearest integer.

Step six, 55, determines the cycle number n* in which two of the center points CP and CP' are closest in time. This is accomplished by repetitive subtractions and comparisons of the absolute magnitudes of the differences between each center point for the respiratory motion with each center point for the cardiac motion for the calculated T cycles.

The identified cycle n* is then used to determine an acquisition start time AS in step seven, 56, according to the formula: $AS = t_1(n) + P + M_a + \frac{1}{2}(AP - QP) + P \cdot (n* - n)$.

Many modifications and variations of the preferred embodiment which will still be within the spirit and scope of the invention will be apparent to those with ordinary skill in the art. For example, other transducers may be used to obtain the reference data on the physiological motion of the body during the scan. Also, more elaborate techniques could be used to predict the timing and coincidence of future motion cycles including second and third order weighting techniques. To the extent that one periodic motion, such as respiration, may be subject to voluntary control, visual feedback may be provided to the patient to better coordinate the control of the voluntary periodic motion with involuntary periodic motion. Further, the techniques described need not be performed in real time but may be applied to data stored from a continuous set of acquired projections to select the subset of those projections that would yield an image with reduced motion artifacts. Under such circumstances parameters such as the period of the motion P need not be estimated from past data but may be measured directly from the data collected on the cycle of interest. Further, these motion artifact reducing techniques are applicable to so called "slip ring" scanning systems where the gantry does not stop and start after each projection set is acquired. In such machines, the angle of acquisition is coordinated with the periodic motion not by stopping the gantry at a preselected point, but by regulating the rotational speed of the gantry between projections to bring it into proper alignment at the correct time. Thus the invention is not limited to the preferred embodiment but is defined by the claims which follow.

We claim:

1. A method for reducing image artifacts in an image object resulting from periodic motion of the object, where the image is produced from a projection set taken continuously during an acquisition period along a plurality of projection axes about the object, the periodic motion having a quiescent period during which the periodic motion is at a minimum, the quiescent period being less than the acquisition period, said method comprising:

produce a signal indicative of said periodic motion;

producing a series of reference signals which indicate a pre-established point in each of a series of said periodic motions;

relating the quiescent period to the pre-established point in each reference signal;

starting the acquisition period at a time related to the reference signal so that the acquisition period for the projection set is centered around the quiescent period.

2. The method described in claim 1 wherein the periodic motion is respiratory motion.

3. The method described in claim 1 wherein the periodic motion is cardiac motion.

4. A method for reducing image artifacts resulting from periodic motion of an object, where the image is produced from a set of projections taken along a plurality of projection axes about the object, said method comprising:

identifying a principal axis of the periodic motion;

controlling the sequence of projection axes so that the range of projection axes is centered on an angle perpendicular to the principal axis of the periodic motion.

5. A method for reducing image artifacts resulting from a primary periodic motion and at least one secondary periodic motion of an object, where the image is produced from a set of projections taken along a plurality of projection axes about the object, said method comprising:

producing a signal indicative of each said periodic motion;

producing a series of reference signals for each said periodic motion which indicate pre-established points in each cycle of said periodic motions;

identifying centerpoints in quiescent periods related to the pre-established points in each reference signal;

examining a predetermined time interval of the primary periodic motion to identify a quiescent period, related to the reference signal for the primary periodic motion, in which the centerpoints among the primary and secondary periodic motions are closest;

starting the acquisition of projections at a time related to the primary periodic motion's reference signal so that the total acquisition time for one projection set is centered in the identified quiescent period.

6. The method described in claim 5 including the additional steps of:

identifying a principal axis of the periodic motion;

controlling the sequence of projection axes so that the range of projection axes are centered on an angle perpendicular to the principal axis of the periodic motion.

7. An apparatus for producing tomographic images of objects with periodic motion, where each image is reconstructed from a set of projections acquired from detectors on a rotating gantry, the apparatus comprising:

a transducer producing a signal indicative of said periodic motion;

a detector producing a series of reference signals which indicate a preestablished point in each of a series of said periodic motions;

a computer means for identifying a quiescent period related to the pre-established point in each reference signal;

a gantry controller means for starting the acquisition of projections at a time related to the reference signal so that the total acquisition time for one projection set is centered in the quiescent period.

8. A method for reducing image artifacts in an image of an object resulting from periodic motion of the object, where the image is produced from a projection set of projections acquired during an acquisition period along a plurality of projection axes about the object, the periodic motion having a quiescent period during which the periodic motion is at a minimum and the quiescent period being less than the acquisition period, said method comprising:

producing a signal indicative of said periodic motion;

producing a series of reference signals which indicate a pre-established point in each of a series of said periodic motions;

relating the quiescent period to the pre-established point in each reference signal;

starting the acquisition of projections at a time related to the reference signal and preceding the quiescent period by no less than than half of the length of the acquisition period;

ending the acquisition of projections at a time related to the reference signal and succeeding the quiescent period by no less than half the length of the acquiescent period; and selecting a continuous subset of projections from the acquired projections to form the projection set so that the acquisition period is centered around the quiescent period.

* * * * *